(12) United States Patent
Rabal

(10) Patent No.: US 6,840,768 B1
(45) Date of Patent: Jan. 11, 2005

(54) DENTAL DEVICE

(76) Inventor: Jennifer L. Rabal, 1016 Meridith Dr., Terrell, TX (US) 75160-5023

(*) Notice: Subject to any disclaimer, the term of this patent is extended or adjusted under 35 U.S.C. 154(b) by 169 days.

(21) Appl. No.: 10/156,465

(22) Filed: May 28, 2002

Related U.S. Application Data

(63) Continuation-in-part of application No. 09/704,065, filed on Nov. 1, 2000, now Pat. No. 6,394,805.
(60) Provisional application No. 60/164,425, filed on Nov. 9, 1999.

(51) Int. Cl.$^7$ .................................................. A61C 3/16
(52) U.S. Cl. ........................................ 433/159; 81/423
(58) Field of Search ........................ 433/4, 159, 160; 81/418, 423

(56) References Cited

U.S. PATENT DOCUMENTS

| | | | | |
|---|---|---|---|---|
| 491,515 A | * | 2/1893 | Blake | 433/159 |
| 753,456 A | * | 3/1904 | Weidinger | 7/133 |
| 1,487,776 A | | 3/1924 | Goldberg | |
| 1,626,226 A | | 4/1927 | Cantor | |
| 1,670,361 A | * | 5/1928 | Johnson | 433/23 |
| 2,504,227 A | | 4/1950 | Rubba | |
| 2,592,641 A | | 4/1952 | Balderstone | |
| 2,674,800 A | * | 4/1954 | Osborn et al. | 433/159 |
| 2,725,637 A | | 12/1955 | Rabben | |
| 2,959,858 A | * | 11/1960 | Drake | 433/4 |
| 3,209,458 A | * | 10/1965 | Rosen | 433/145 |
| 3,834,026 A | * | 9/1974 | Klein | 433/159 |
| 3,986,265 A | * | 10/1976 | Cusato | 433/4 |
| 4,040,186 A | | 8/1977 | Kalvelage | |
| 4,189,839 A | * | 2/1980 | Manuel | 433/4 |
| 4,697,483 A | | 10/1987 | Rodgers | |
| 4,776,791 A | * | 10/1988 | Hannula et al. | 433/4 |
| 5,044,954 A | * | 9/1991 | Lukase et al. | 433/159 |
| 5,182,841 A | | 2/1993 | Park et al. | |
| 5,538,421 A | | 7/1996 | Aspel | |
| 5,833,460 A | | 11/1998 | Maeda | |
| 5,893,876 A | | 4/1999 | Turkel et al. | |
| 6,413,088 B1 | * | 7/2002 | Kawaguchi | 433/159 |

* cited by examiner

*Primary Examiner*—Ralph A. Lewis
(74) *Attorney, Agent, or Firm*—Chauza & Handley, LLP; Roger N. Chauza

(57) ABSTRACT

A dental device for removing an onlay or crown from a patient's tooth. The device includes pliers-type handles for operating a corresponding pair of tips. The tips are equipped with grips adapted for holding an onlay or crown therebetween. The grip edges have a number of rounded projections that are effective to firmly grip the onlay or crown.

18 Claims, 10 Drawing Sheets

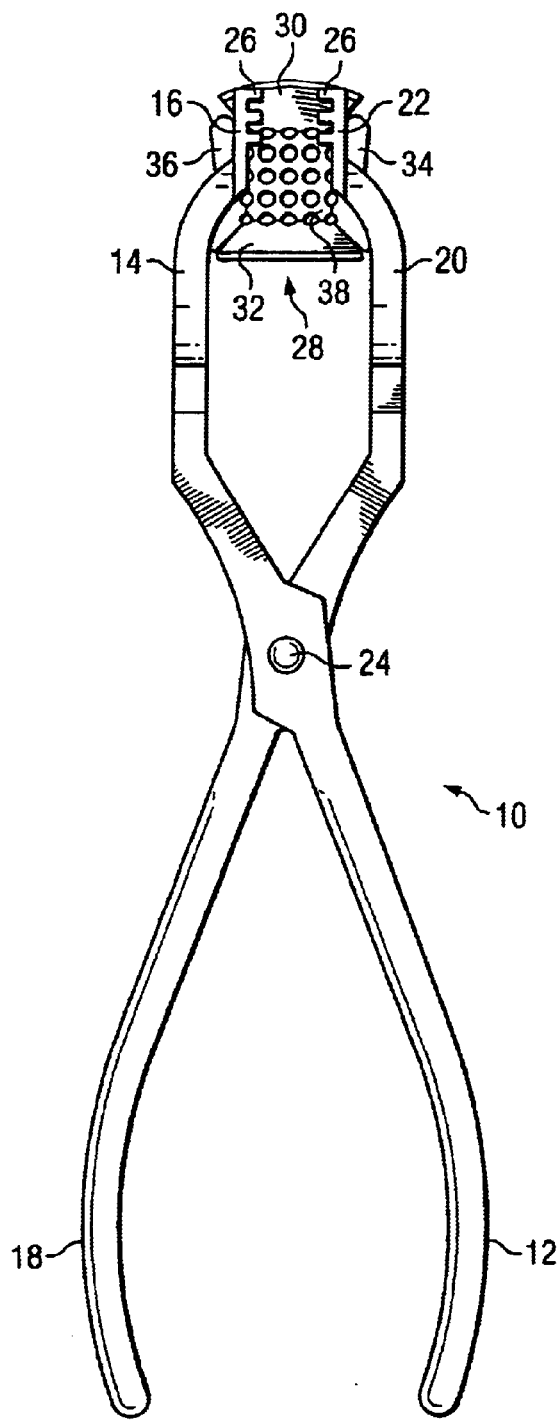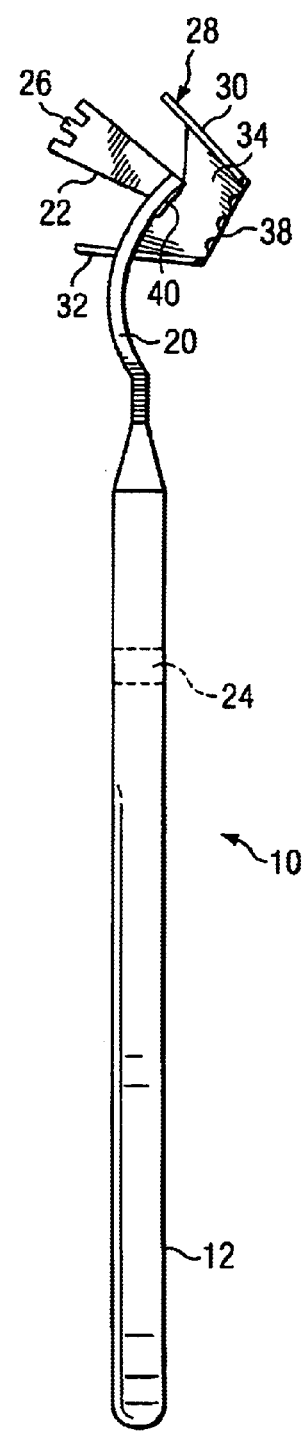
FIG. 1
FIG. 2

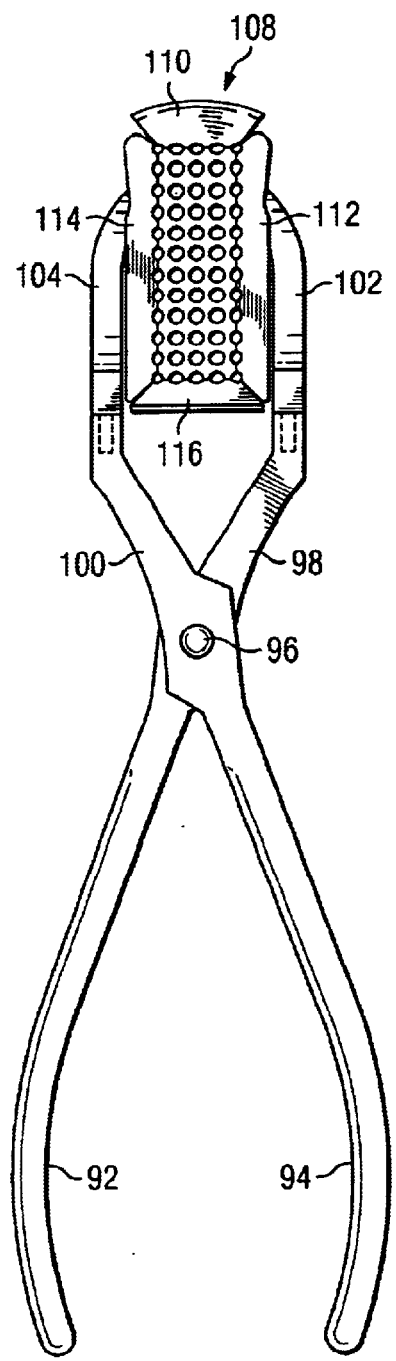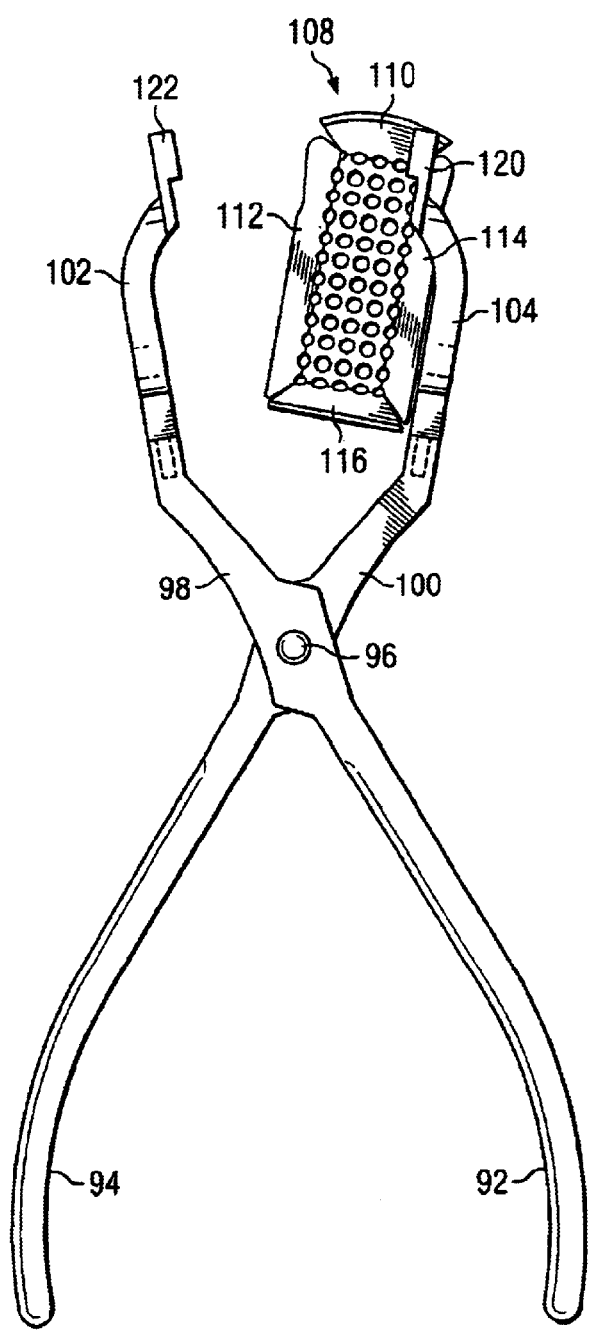
*FIG. 7*
*FIG. 8*

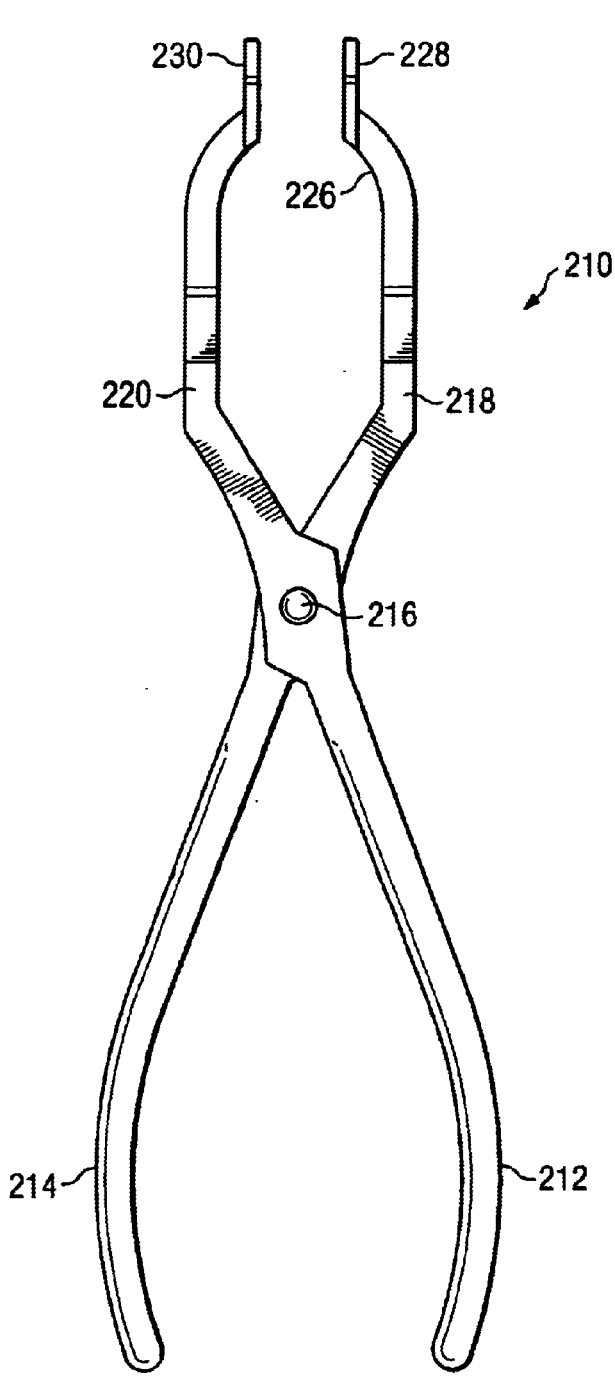
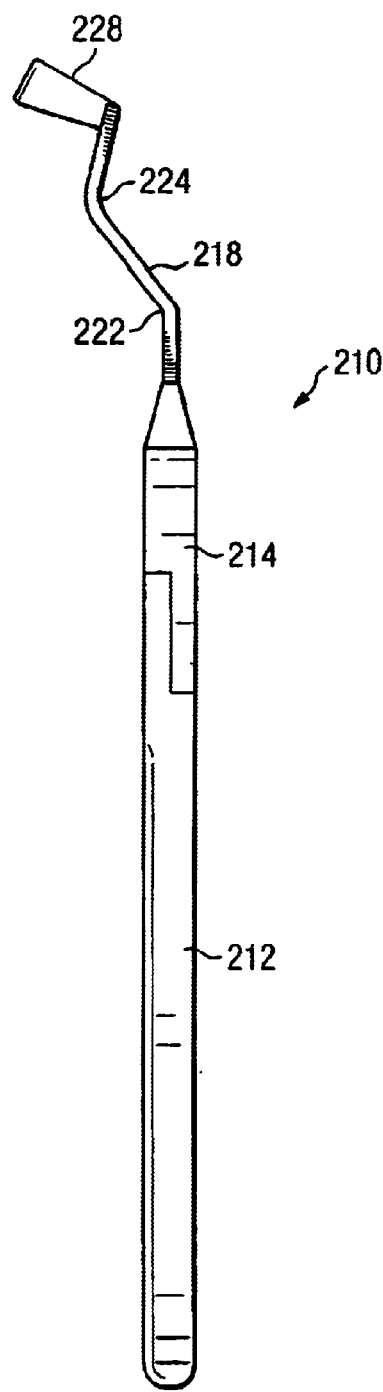
*FIG. 13*  *FIG. 14*

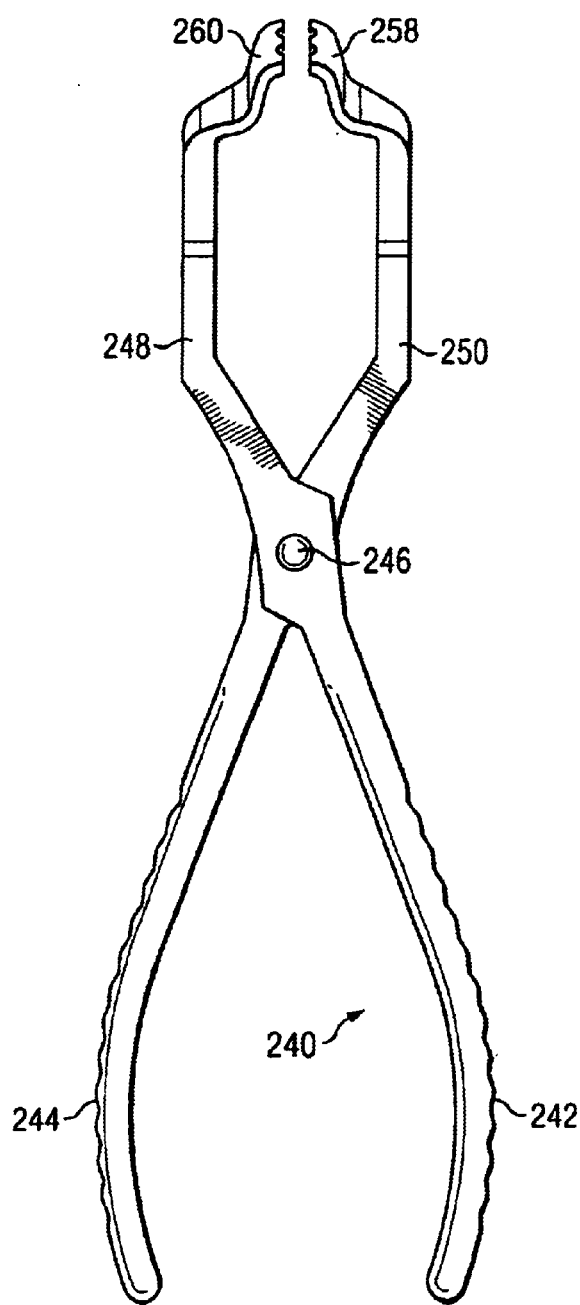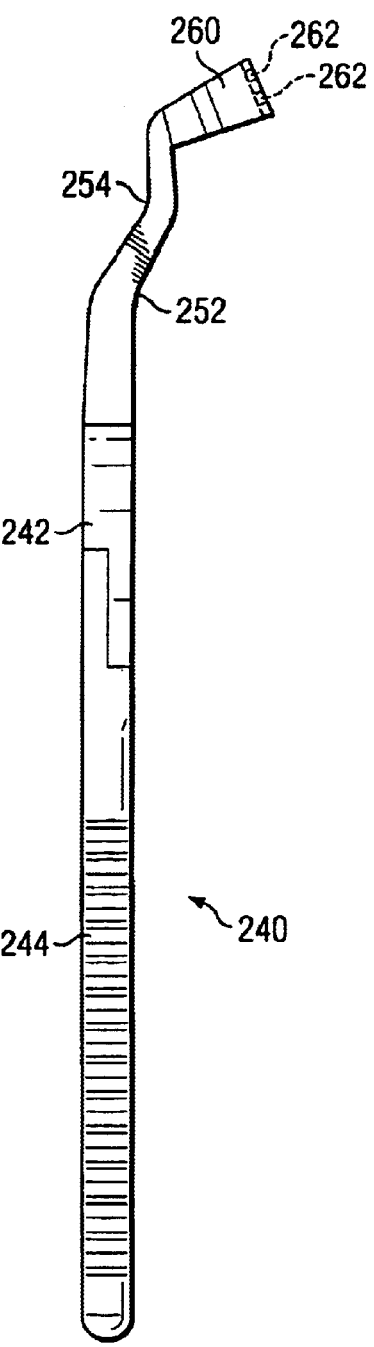
*FIG. 15*  *FIG. 16*

DENTAL DEVICE

CROSS-REFERENCE TO RELATED APPLICATIONS

This patent application is a continuation-in-part application of U.S. non-provisional application entitled "DENTAL CROWN REMOVER WITH BASKET," filed Nov. 1, 2000, and accorded Ser. No. 09/704,065, now U.S. Pat. No. 6,394,805, issued May 28, 2002, which claims the benefit of U.S. Provisional Application entitled "Dental Crown Remover," filed Nov. 9, 1999 and accorded Ser. No. 60/164,425. The entire disclosures of the prior related applications are incorporated herein by reference.

TECHNICAL HELD OF THE INVENTION

This invention relates in general to dental devices, and more particularly to the type of devices for use with onlays and crowns.

BACKGROUND OF THE INVENTION

Significant advances have been made in the last few decades in the care and treatment of people's teeth. Not only are there a host of personal teeth care appliances and teeth cleaning agents, but significant advances have also been made in the general practice and general dentistry field. It has become a common practice to repair teeth by placing a crown, onlay or artificial tooth structure over the existing (remaining) nondecayed structure. The original tooth is generally prepared by grinding a major portion of the tooth away, leaving only the remaining structure. A mold is made of the prepared tooth structure, so that a crown or onlay can be fabricated. In the meantime, the patient is fitted with a temporary crown so that normal chewing functions can be carried out during the time in which the permanent crown is made. A crown remover of this type is described in detail in U.S. Pat. No. 3,834,026.

During the procedure in fitting the temporary crown and grinding the original tooth structure, numerous attempts are generally made to fit the temporary crown on the remaining tooth structure, as far as height and concavity are concerned. In doing so, various types of pliers and other appliances have been constructed so as to firmly grip the temporary crown for placement on the remaining tooth structure. The pliers generally include a rounded set of jaws to firmly grip the crown so as to fit it on the remaining tooth structure, as well as remove it for grinding adjustments to either the remaining tooth structure or the temporary crown.

Frequently, in the placement or removal of the temporary crown or onlay from the remaining tooth structure, the crown or onlay inadvertently loses its grip from the pliers, and falls or otherwise becomes dislodged in the patient's mouth. In other more serious occurrences, the patient can inadvertently swallow or aspirate the crown or onlay. This is especially troublesome when the crown/onlay fitting operation is carried out on the upper teeth of a patient. The occurrences with which the temporary crowns or onlays are inadvertently dropped in the patient's mouth are frequent during the training of dental students.

Pliers-type appliances that are forged to be short are not often used for the reason that they cannot easily access a patient's teeth with an unobstructed view, especially the posterior teeth.

It is well known that a crown replaces the entire biting surface of the patient's tooth. In order to prepare a tooth for a crown, a large portion of the enamel and dentin is removed. An onlay, on the other hand, can be used to repair the cusp portions of the biting surface of a tooth. An onlay is bonded on the top of the biting surface that was damaged or decayed. Because the onlay is a smaller structure, as compared to a crown, different types of grips on dental devices are necessary to firmly grip the structure so that it can be reliably installed or removed from the tooth.

It can be seen from the foregoing, that a need exists for a technique for easily recovering a dropped crown so that it does not fall in the patient's mouth. Another need exists for a dental appliance that is long and forged for easier access and that is equipped with a basket for catching a dislodged crown to prevent it from falling into the patient's mouth. Another need exists for a dental appliance that can deflect or catch a crown, onlay or other similar device dislodged from the dental appliance. Another need exists for a crown remover that allows easier access in a patient's mouth to posterior teeth for attaching and removing a crown thereon. Yet another need exists for various crown grips shaped to facilitate the removal of crowns. An additional need exists for a crown remover adapted for removably attaching various tips thereto, where the tips have different shaped crown grips.

SUMMARY OF THE INVENTION

In accordance with the principles and concepts of the invention, there is disclosed a dental appliance for reducing those occurrences in which a dislodged or dropped onlay falls within the patient's mouth. According to a preferred embodiment of the invention, a pliers appliance includes a pair of handles that can be gripped by the dentist, with jaws at the opposing ends shaped to conform to the onlay curvature to firmly grip the same. In accordance with an important feature of the invention, a tip of the appliance is constructed to include a grip that is shaped to grasp an onlay for applying or removing the same with respect to a patient's tooth. The onlay tip of the of one embodiment is planar so that the shape thereof can grip the onlay structure without the tooth itself interfering with installing or removal of the onlay on the tooth. In another embodiment, the outer edges of the grips have a number of rounded protrusions that are effective to firmly grip an onlay.

In accordance with another embodiment, the device includes a grip that are generally planar and extend outwardly along the longitudinal axis of the device. The grips are then angled inwardly toward each other, with edges that abut together when the device is closed upon itself. The inward turned edges allow the dentist to engage the artificial tooth structure under a peripheral edge thereof so that pressure can be applied in the removal of the structure from the patient's tooth. In this manner, the dentist does not have to apply a substantial amount of squeezing pressure on the artificial tooth structure during removal thereof from the patient's tooth. The inward turned edges of each grip include one or more indentions formed therein to facilitate gripping with the artificial tooth structure when holding the same between the grips.

In accordance with another embodiment, the grips can be formed or coated with a non-metallic material, such as being rubber or plastic coated, or formed with a hard synthetic material such as nylon, carbon fiber or other rugged non-metallic material. The rubber coating for the grips can be removed therefrom and appropriately disposed of. As an alternative, the metallic tips can be formed with inlaid plastic or synthetic material to eliminate any metal-to-metal contact with artificial tooth structures, such as titanium implants.

The many embodiments may include various tips removably attached thereto, where each tip can have a different shaped grip. The various attachable grips are shaped to facilitate different shaped crowns, onlays, etc.

BRIEF DESCRIPTION OF THE DRAWINGS

Further features and advantages will become apparent from the following and more particular description of the preferred and other embodiments of the invention, as illustrated in the accompanying drawings in which like reference characters generally refer to the same parts, components, elements or functions throughout the views, and in which:

FIG. 1 illustrates a top view of the crown remover constructed according to one embodiment of the invention;

FIG. 2 illustrates a side view of the crown remover shown in FIG. 1;

FIG. 7 illustrates a bottom view of the embodiment shown in FIG. 6;

FIG. 8 illustrates a top view of the embodiment shown in FIG. 6, with the gripping tips shown separated, and removable from the pliers;

FIG. 13 is a front view of one embodiment of a dental device constructed with grips adapted for use with onlays;

FIG. 14 is a side view of the dental device of FIG. 13;

FIG. 15 is a front view of another embodiment of a dental device having grips adapted for use with onlays, as well as crowns;

FIG. 16 is a side view of the dental device of FIG. 15;

DETAILED DESCRIPTION OF THE INVENTION

Figure 3:
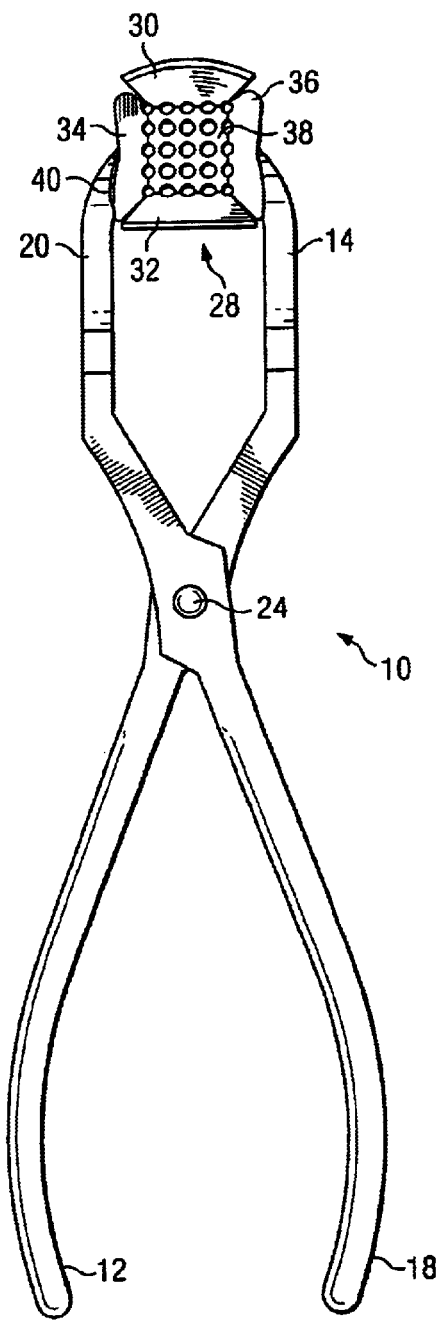
FIG. 3 illustrates a bottom view of the crown remover shown in FIG. 1.

FIGS. 1–4 illustrate various views of the crown remover constructed according to one embodiment of the invention. As used herein, the term "crown" also encompasses the term only, bridge and other fixtures that are applied to a patient's teeth or other tissue. The crown remover 10 includes a pliers-type appliance, having a first member defined by a handle 12 at one end and a tip 14 at the other end. The end of the tip 14 is equipped with a crown grip 16. The other member similarly includes a handle 18, a tip 20 and a crown grip 22. The first member and second member are pivotally joined at respective midsections thereof, by a screw 24, rivet, pin or other pivotal or hinging mechanism. As is conventional with pliers-type tools, the handles 12 and 18 can be manipulated by the user to open and close the tips 14 and 20. The crown grips 16 and 22 are adapted for firmly gripping the crown to both attach it on the margin structure, and remove it therefrom. As noted above, this is especially important for use in fitting temporary crowns until the permanent crown can be applied next to the tooth margin structure. The crown grips 16 and 22 each include plural fingers 26 at the ends thereof to provide a certain degree of flexibility in gripping the crown. The fingers 26 of each of the crown grips 16 and 22 are angled inwardly toward each other. This facilitates the removal of a temporary crown by allowing the inwardly bent fingers 16 to grasp the marginal edge of the crown. When pulled, the crown is more firmly grasped for removal.

Figure 4:
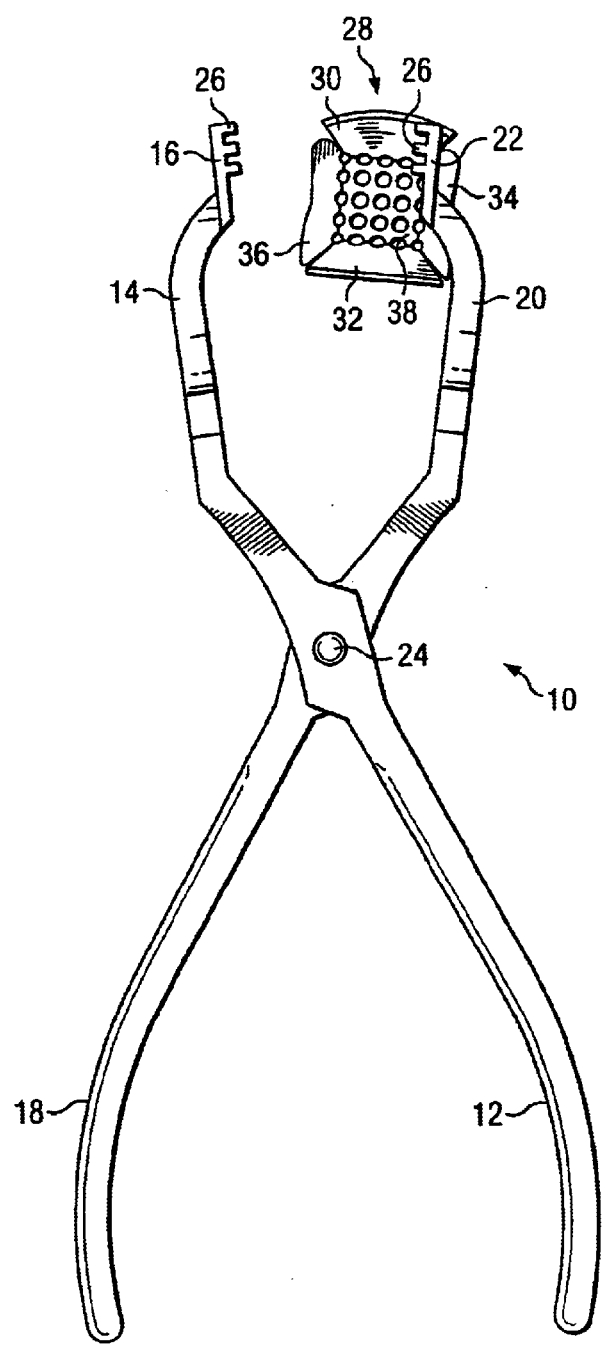
FIG. 4 illustrates a top view of the crown remover shown in FIG. 1, but with the gripping tips shown separated.

In accordance with an important feature of the invention, one of the tips 14 or 20 is equipped with a container or basket 28 that moves with the tip as the crown remover 10 is manually manipulated. In the preferred form, the basket 28 is fastened to the tip 20. The basket 28 is constructed with four sidewalls that slant or taper outwardly as shown in FIG. 2. The front and back sidewalls 30 and 32 are somewhat taller or higher than the other sidewalls 34 and 36, as shown in FIGS. 2 and 4. While not shown, the front sidewall 30 can be constructed with an inward turned lip (not shown) along the top edge thereof to help maintain a dislodged crown contained within the basket 28. The lip can be formed with an internal angle, with respect to the frontal sidewall 30, of about 45 degrees. Each of the four sidewalls 30–36 of the basket 28 is joined at the bottom edges thereof to a basket bottom 38 which is perforated so as not to be water tight. While the basket 28 constructed according to the illustrated embodiment of FIGS. 1–4 is generally rectangular shaped, other shapes can be utilized with equal effectiveness. For example, square, round, oval and other shapes of baskets can be utilized.

When viewing the crown remover 10 from the top, as shown in FIG. 1, the tip 20 is welded or otherwise bonded to the right-hand sidewall 34 of the basket 28. The weld is placed in the area shown in FIG. 2 by reference numeral 40. With this construction, the basket 28 is fixed to one tip 20 and moves therewith, as shown in FIG. 4. The basket 28 can be attached to the tips 20 by other means, such as by the use of screws inserted in holes in the basket, and tightened in threaded holes in the tip 20. In other arrangements, the basket can be fixed to the crown grip 22, or to the other tip 14 or grip 16.

With reference again to FIGS. 1 and 2, the basket 28 is generally larger than the crown grips 16 and 22. Hence, should the crown fall, it has a better chance of dropping into the basket 28. The pliers appliance 10 is not limited to use in attaching crowns or onlays on a patient's upper teeth, but also the lower teeth. In this latter instance, the basket 28 can function to deflect a crown that is propelled upwardly when attaching or removing the same. While the basket 28 cannot catch and hold a crown when inverted, such as when used on a patient's bottom teeth, the basket 28 can deflect a propelled crown so that it does not enter the patient's air passageways.

The crown remover 10 is preferably constructed by forging techniques with a stainless steel or other suitable material. The crown remover 10 can thus be sterilized by conventional sterilization equipment.

In operation, a dentist can open the tips 14 and 20 of the pliers appliance 10 and insert a permanent or temporary crown, or onlay, between the crown grips 16 and 22. Holding the crown firmly between the grips 16 and 22 by applying pressure to the handles 12 and 18, the dentist can engage the crown with the margin structure previously prepared. The crown remover 10 is particularly advantageous when attaching permanent or temporary crowns in the top teeth of a patient. In this instance, should the crown fall, become dislodged or otherwise disengaged from the tooth structure, and falls, the basket 28 will catch the crown and prevent its falling into the patient's mouth. In the event a temporary crown has been applied to the tooth structure, and needs removal thereof, the dentist can grasp the temporary crown with the crown grips 16 and 22 and wiggle the temporary crown until it becomes loosened from the tooth structure. Again, should the temporary crown either become dislodged from the grips 16 and 22, or should it break into pieces, the crown, tooth or parts thereof will fall into the basket 28. This is highly important in preventing parts of the crown or tooth from falling into the patient's mouth, or down the patient's throat with the possible risk of being aspirated into the lungs. The appliance 10 is utilized in the same manner with permanent crown or onlays.

Figure 5A:
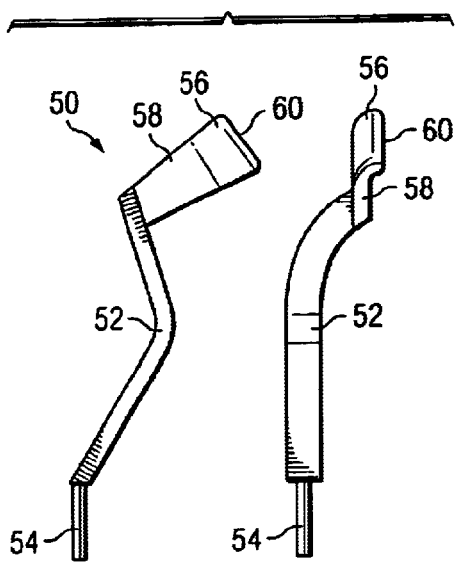
FIGS. 5a–5d illustrate various embodiments of crown grips, each adapted for gripping different types of crowns.

FIGS. 5a–5d illustrate different tips adapted for use with the invention. The various tips are adapted for being removably attached to the dental appliance described below. FIG. 5a illustrates one embodiment of a crown remover tip 50 in a side view shown at the left of the drawing, and taken orthogonal thereto in the right of the drawing. The tip 50 includes the dog-leg tip 52 having an end 54 removably attached to the pliers. The dog-leg tip 52 provides better access to the posterior teeth of a patient. In addition, a better unobstructed view of the teeth is provided, even with the appliance positioned in the patient's mouth. At the other end of the tip 52 is a crown grip 56. The grip 56 includes a generally planar blade 58 with an end 60 that is bent or otherwise curved inwardly to capture the crown. With this arrangement, the grip 56 can engage the crown and partially envelope the same.

Figure 5B:
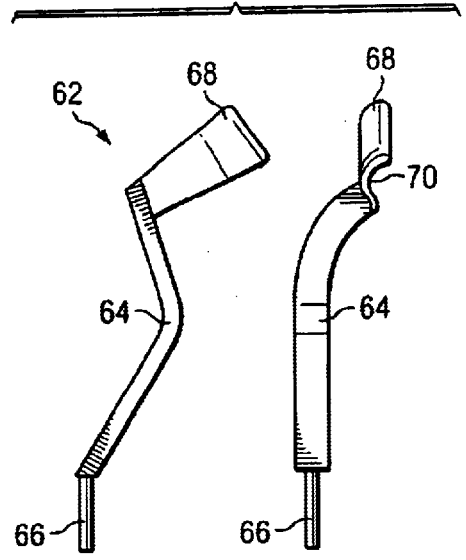

FIG. 5b illustrates another embodiment 62 having a dog-leg tip 64 with an end 66 that is removably attached to the dental device. The crown grip 68 is generally shaped with a concave inside surface 70 to again envelope and grip the crown.

Figure 5C:
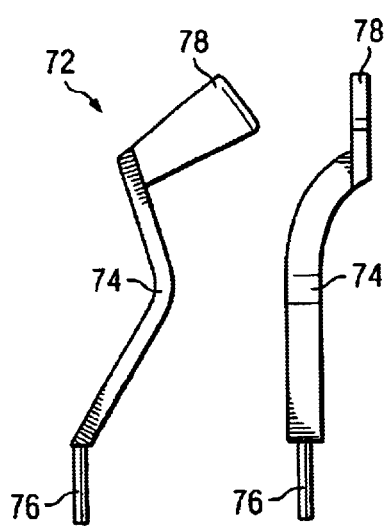

FIG. 5c illustrates yet another embodiment of a tip 72. The tip 72 includes a dog-leg mid-section 74 and an end 76 that is constructed to be removably attached to the dental device. A crown grip 78 is constructed so as to be generally planar. This embodiment is well adapted for use with onlays to firmly grip the same.

Figure 5D:
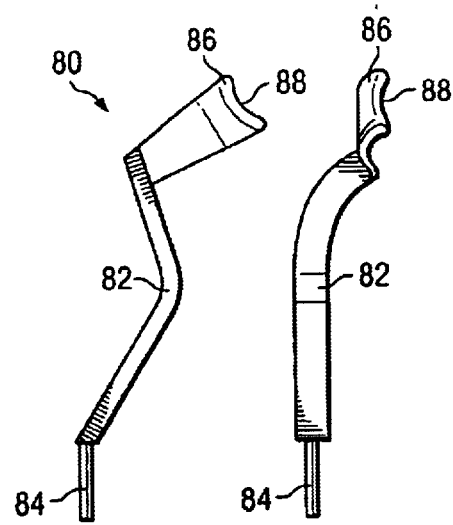

FIG. 5d illustrates yet another embodiment of a tip 80. The tip 80 includes a dog-leg shaped mid-section 82 with an end 84 that is removably attachable to the dental device. The crown grip 86 is much like that shown in FIG. 5b, but includes an end 88 that is curved inwardly. This curved end 88 facilitates the manipulation of a crown with respect to other teeth in the patient's mouth.

In all of the embodiment of the various tips shown in 5a–5d, such tips can be utilized in combination with a basket structure described below, both of which are removably attached to the dental device.

Figure 6:
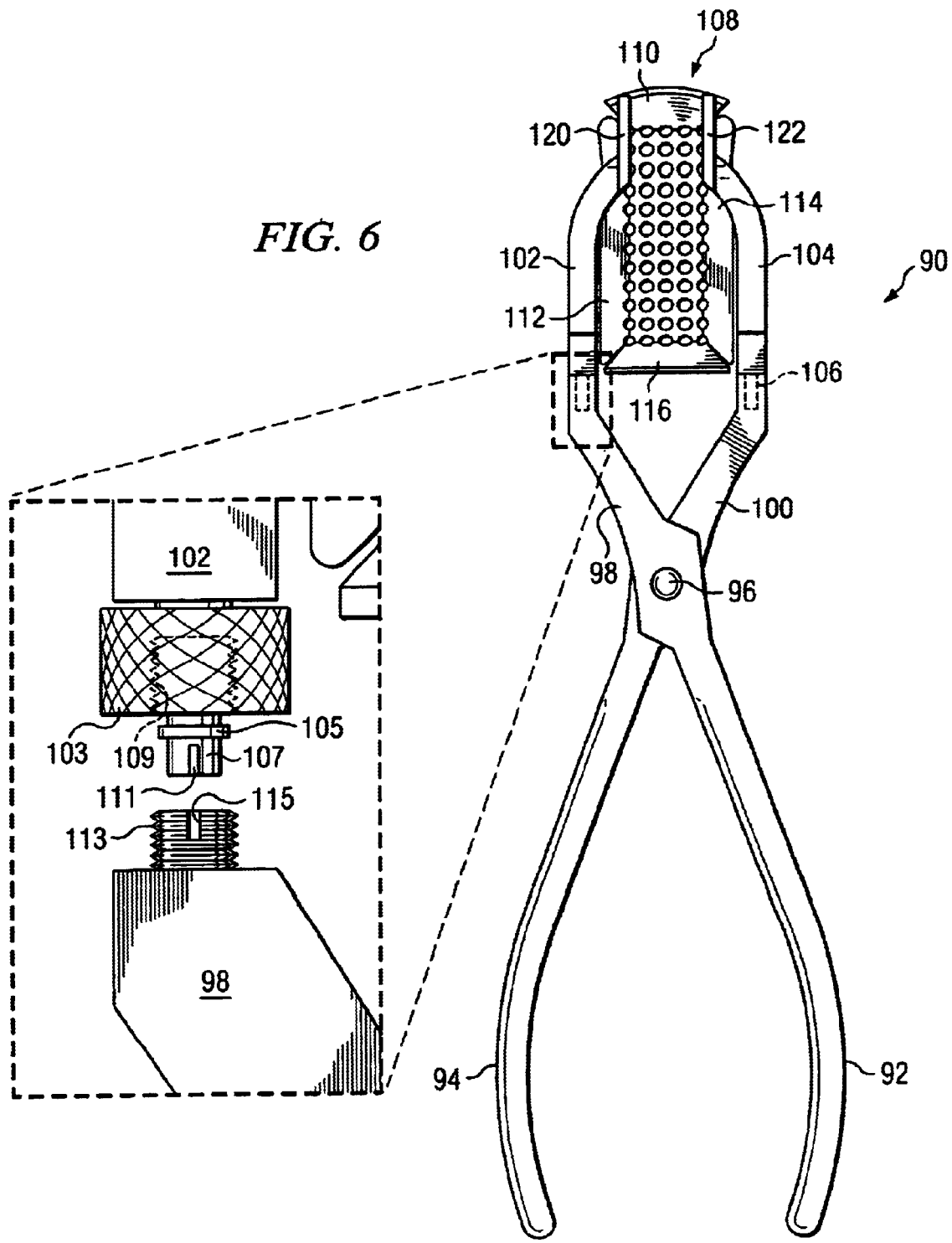
FIG. 6 illustrates atop view of a crown remover constructed according to another embodiment of the invention, in which the gripping tips are removably attached to the pliers, and showing in the enlargement the mechanism allowing the parts to be removably attached together.

With reference now to FIGS. 6–8, there is illustrated another embodiment of the dental device constructed according to the principles and concepts of the invention. The dental device 90 is constructed as a pliers-like appliance having handles 92 and 94 pivotally connected together by a screw 96, or the like. Connected at a working end of the handle 92 is a shortened tip 98. In like manner, connected to the working end of the other handle 94 is a shortened tip 100. Corresponding tip extensions 102 and 104 are connected respectively to the shortened tips 98 and 100. The mechanism for removably attaching the tip extensions to the respective shortened tips is diagrammatically shown as reference numeral 106. Both tip extensions 102 and 104 are removably attached to the pliers appliance 90 in the same manner. Fastened to one tip extension is an elongate basket 108, shown in FIG. 8 connected to tip extension 104. The basket 108 is constructed substantially identical to that shown in FIGS. 1–4, except the basket 108 is rectangular-shaped. The end sidewall 110 is longer than the other sidewalls 112–116. This facilitates capturing of a dropped or dislodged crown so that it is not directed toward the patient's throat. The dental device 90 otherwise functions in a manner much like that described above in connection with FIGS. 1–4. The crown grips 120 and 122 can be any of the types shown in FIGS. 5a–5d or yet other configurations for gripping the particular type of fixture to be fastened or otherwise attached to a patient's tooth. The principles and concepts of the invention can also be utilized for capturing or deflecting body tissue parts while carrying out operations thereon.

The enlargement shown in FIG. 6 illustrates the mechanism which allows the tips 102 and 104 to be removably attached to the corresponding shortened tips 98 and 100. In the preferred form, the mechanism includes a conventional threaded coupling screw arrangement and registration means to maintain alignment between the shortened tip 98 and the appliance tip 102. The removable attachment mechanism includes an internally threaded sleeve 103 on the tip 102. The sleeve 103 is captured on the tip 102 by an annular collar 105 formed integral with the tip 102. The tip 102 has a rib 111 or raised area to provide registration and alignment between the tip 102 and the shortened tip 98. The rib 111 is formed on a stub end 107 of the tip 102. The stub 107 fits within a receptacle 113 formed within the shortened tip 98. The receptacle 113 has formed therein a registration slot 115 for receiving therein the rib 111 of the tip 102. The outer surface of the receptacle 113 is threaded for engagement with the internal threads 109 of the sleeve 103.

The removable attachment mechanism is fastened together by aligning the rib 111 with the slot 115, and then sliding the stub 107 into the bore of the receptacle 113 until the collar 115 engages with the frontal edge of the receptacle 113. Then, the sleeve 103 is threadably engaged with the outer threads of the receptacle 113 until tight. This secures the tip 102 to the shortened tip 98 and prevents rotation therebetween.

Many other releaseable attachment mechanisms can be utilized with equal effectiveness. For example, the stub 107 can be square for fitting within a square bore of the receptacle 113.

Figure 9:
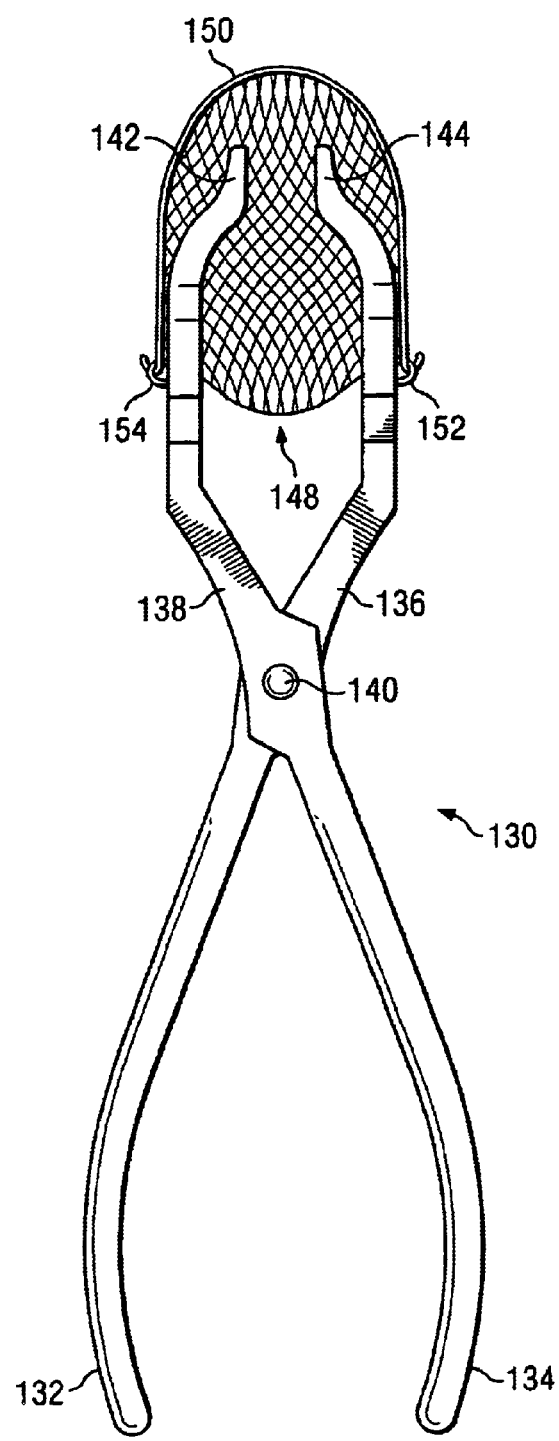
FIG. 9 is a top view of yet another embodiment of the dental device, equipped with a wire mesh basket.

FIG. 9 illustrates yet another embodiment of the invention. Here, a pliers-type appliance 130 includes a pair of handles 132 and 134 connected to respective tips 136 and 138 via a pivot pin 140. Formed at the end of the tips 136 and 138 are respective crown grips 144 and 142. In this embodiment a flexible mesh basket 148 is fastened to the tips 136 and 138. The wire mesh is preferably constructed of a metallic link-type of flexible mesh. The support wire loop 150 and the mesh basket can both be formed with stainless steel material. The peripheral edge, or opening, of the wire mesh basket 148 is supported by a flexible support wire loop 150. The support wire loop 150 has ends that are hooked for engagement within corresponding loops 152 and 154 welded to the outer sides of the tips 136 and 138. With this arrangement, when the crown grips 142 and 144 are opened or closed, the mesh basket 148 flexes accordingly. In addition, the ends of the wire support 150 engaged within the loops 152 and 154 are not completely closed, thereby allowing the wire mesh basket 148 to be removed. If the removability of wire mesh basket 148 is of secondary importance, then the ends of the wire support 150 can be welded or otherwise bonded to the sides of the tips 136 and 138.

Figure 10:
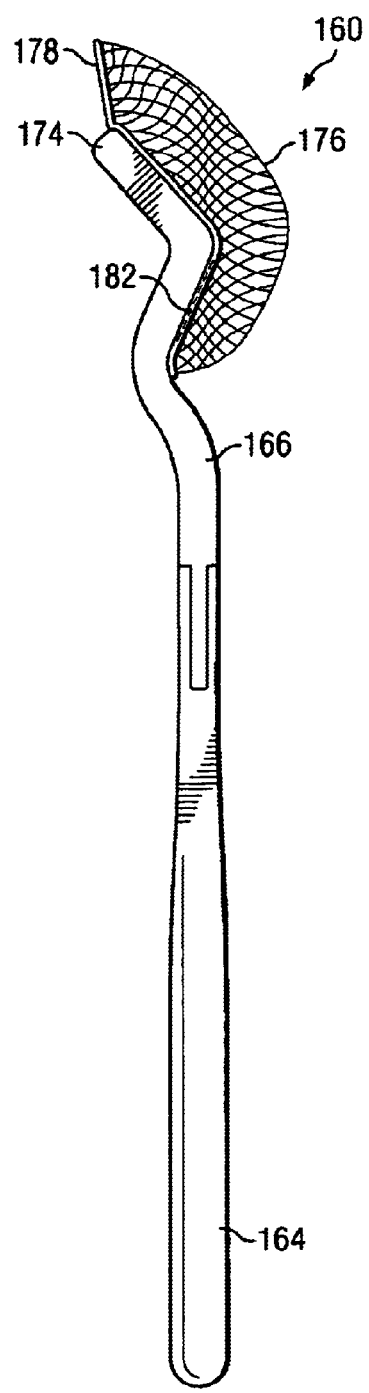
FIGS. 10 and 11 are respective side and bottom view of yet another embodiment of the dental device constructed according to the invention.
Figure 11:
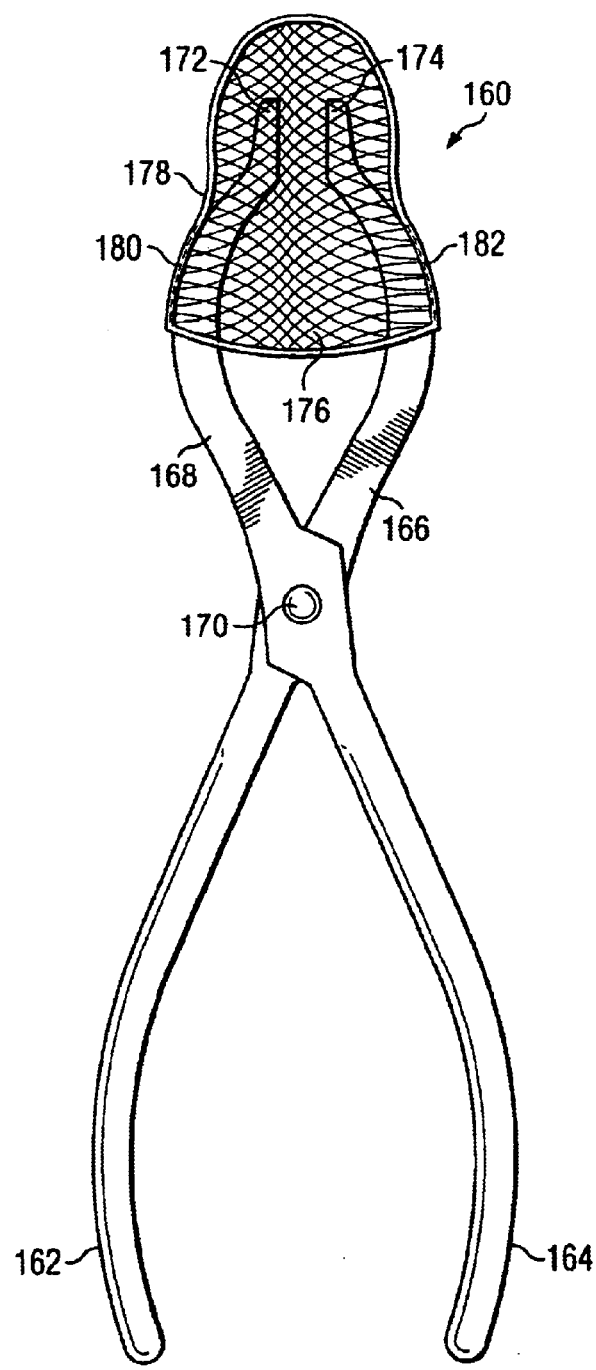

FIGS. 10 and 11 illustrate yet another embodiment of a crown remover 160. The crown remover 160 of this embodiment includes a pair of pliers-type handles 162 and 164 coupled to respective tips 166 and 168, via a pivot pin 170. Formed integral with the tips 166 and 168 are corresponding crown grips 172 and 174. A flexible mesh basket 176 has an opening supported by a wire loop 178 formed in the shape shown in FIGS. 10 and 11. The opening of the wire mesh basket 176 is welded or otherwise fixed to the wire loop 178. In addition, the wire loop 178 is welded to the tips 166 and 168 at locations 180 and 182. With this construction, the wire mesh basket 176 is fixed to the tips 166 and 168 of the device 160 and thus, moveable therewith when the device 160 is manipulated to open and close the grips 172 and 174. Other shapes of the basket 176 and wire loop 178 can be constructed for adapting it to various shapes of tips 166 and 168.

Figure 12:
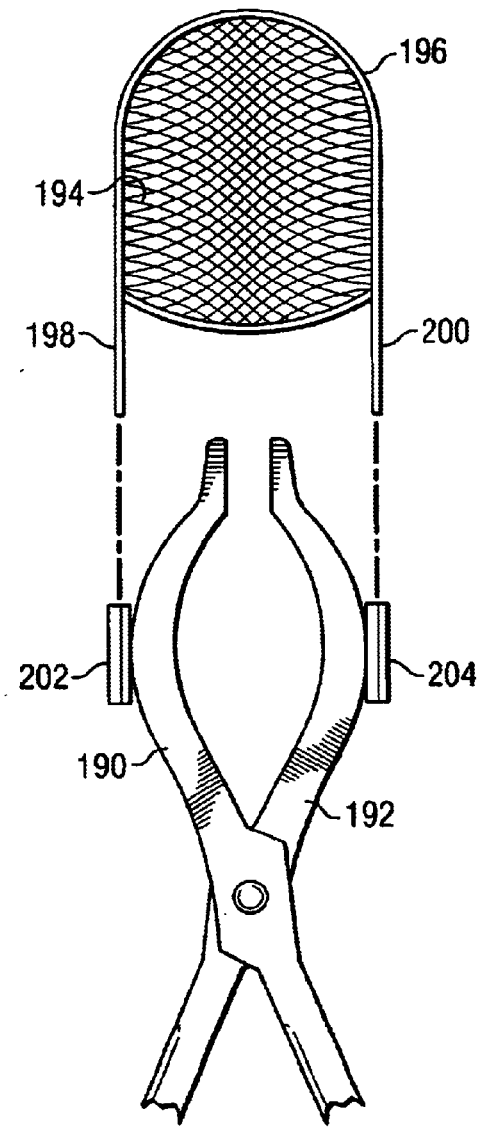
FIG. 12 is a top view of a portion of the dental device, constructed with a wire mesh basket removably attached thereto.

FIG. 12 illustrates another embodiment of the dental device according to the invention, in which there is provided a pair of tips 190 and 192, coupled to a plier-type device (not shown). A flexible wire mesh basket 194 has an opening or peripheral edge supported by a wire loop 196. The wire loop includes a pair of extensions 198 and 200 that are insertible into corresponding tubular receptacles 202 and 204. The tubular receptacles 202 and 204 are welded or otherwise bonded to the sides of the tips 190 and 192. This construction allows the device to be utilized without the basket 194 or, when the same is required, allows the basket wire ends 198 and 200 to be inserted into the tubular receptacles 202 and 204. Preferably, there is a friction fit between the wire ends 198 and 200 and the corresponding tubular receptacles 202 and 204.

With reference now to FIG. 13, there is illustrated a dental device 210 adapted for use with onlays. The device 210 includes a pair of handles 212 and 214 pivotally connected together near a middle section thereof by a screw 216, rivet, or other hinging mechanism well known to the pliars art. Connected to the upper portion of the handle 214 is a tip 218. Similarly, connected to the upper portion of the other handle 212 is a corresponding tip 220. The tips 218 and 220 are curved at two locations 222 and 224, as shown in FIG. 14 with respect to tip 218. The tips are forged or otherwise formed with a third curve 226, as shown in FIG. 13. With this formation of the tips 218 and 220, the access by the dentist to the various teeth of a patient is facilitated.

Formed integral with the tips 218 and 220 of the device 210 are corresponding grips 228 and 230. As with the tips 72 shown above in connection with the onlay tips 72 of FIG. 5c, the tips 228 and 230 are planar blades, that are angled outwardly to the front to provide ready access and a firm grip to an onlay. The tips 218 and 220 can be removably attached to the respective handles 212 and 214 in the manner noted above, as well as with other removable attachment mechanisms. In addition, the grips can be formed to be removably attached to the tips 218 and 220. Lastly, the device 210 can be equipped with a basket in the manner described above.

Figure 17:
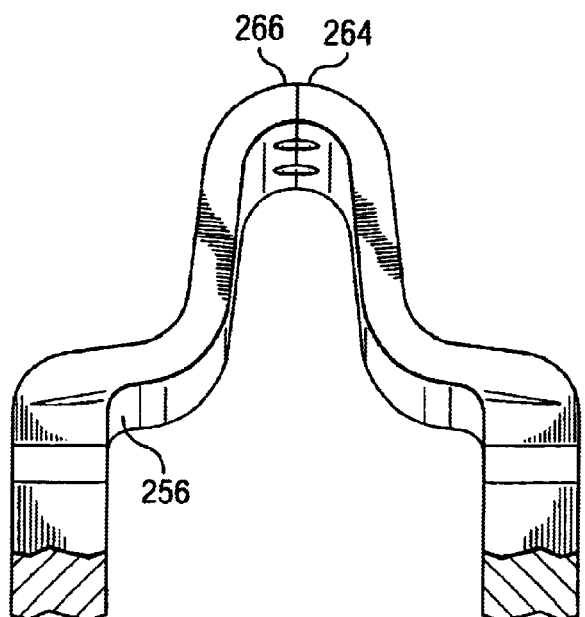
FIG. 17 is an end view of the dental device, as viewed from the top end of the device of FIG. 15, showing the inwardly curved grip ends for gripping onlays and crowns.

FIGS. 15–18 illustrate another embodiment of a device 240 adapted for use with onlays and crowns. The device 240 includes a pair of handles 242 and 244 pivotally connected together with a screw 246. Similar to the other embodiments, the handles 242 and 244 have attached thereto respective tips 248 and 250. The tips are formed with curved sections 252, 254 and 256 much like that shown in the embodiment of FIGS. 13 and 14. In the embodiment of FIGS. 15–17, the grips 258 and 260 are adapted for gripping both a crown and an onlay, depending on the type of artificial tooth structure being used by the dentist at that time. The grips 258 and 260 each have edges that engage with each other when the handles of the device 240 are squeezed together, without an onlay therebetween. The grip edges each have a number of indentions, one 91 shown as reference character 262 in FIG. 16. The indentions 262 function to provide a firm and nonslip grip to a crown or an onlay. The indentions 262 are shown generally as semicircular cutouts formed into the respective edges 264 of the grips 258 and 260. The indentions can also be in the form of curved ripples formed in the edges 264 and 266.

Figure 18:
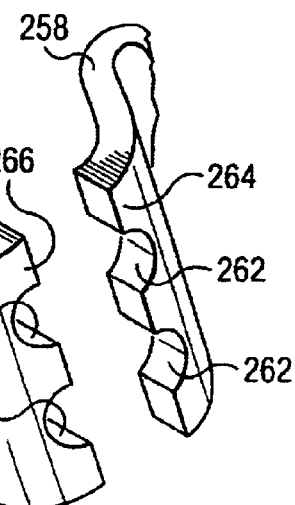
FIG. 18 is an enlargement of the grips of FIG. 17, showing the detail of the gripping edges.

In accordance with an important feature of the invention, the grips 258 and 260 are formed with the edges 264 and 266 turned inwardly, as shown in the enlarged views of FIGS. 17 and 18. The inward turned edges 264 and 266 facilitate the gripping under a crown or onlay for removal thereof from the patient's tooth. In other words, the inward turned edges 264 and 266 can be placed under the peripheral edge of the artificial tooth structure (onlay or crown) to pull it off the tooth, thereby allowing a reduced squeezing pressure to be applied by the dentist to the handles of the device 240. The removed artificial tooth structure is thus less likely to be crushed or cracked from the radial pressure of the grips thereon.

Figure 19:
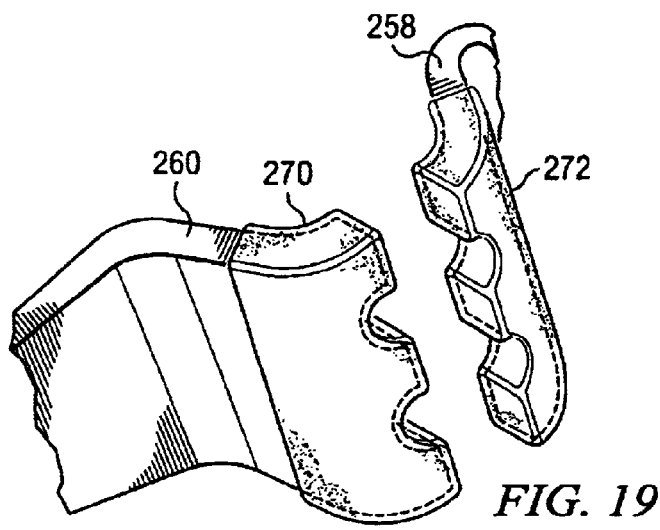
FIG. 19 illustrates the grips of a dental device coated with a non metallic material.

FIG. 19 illustrates the grips 260 and 258 coated with a layer of a non-metallic material, such as rubber or plastic 270 and 272. In some situations, such as working with temporary tooth implants constructed with titanium, such material should not contact the metallic part of the device 240. In this instance, the grips can be coated with the nonmetallic material. The grips 258 and 260 can be dipped in the liquid rubber or plastic. The grips of the device 240 can also be constructed with inlaid plastic in the contact surfaces to prevent a metal-to-metal contact with the titanium implants. In yet other instances, the grips can be made of a nylon or other hard nonmetallic material. Those skilled in the art may find that the plastic or rubber coating formed on the grips can be made disposable. Once the rubber layer on the grips is used, they can be discarded and replaced with new sterile rubber or plastic covers.

Although the preferred and other embodiments have been described in detail, it should be understood that various changes, substitutions and alterations can be made therein without departing from the spirit and scope of the invention as defined by the appended claims.

What is claimed is:

1. A dental device, comprising:
   a pliers having a pair of handles for operating a corresponding pair of tips, said handles attached together about an axis of pivotal movement, and said handles and tips extending generally horizontally and oriented generally perpendicular to said axis of rotation;
   a grip attached to a respective end of each said tip, said grips angled downwardly with an obtuse angle with respect to said handles when said handles are oriented in a horizontal plane;

each said grip formed as a blade of generally uniform thickness, and each said blade being generally parallel to each other;

each said blade terminating with an inwardly turned portion with a blunt edge, the blunt edges of the inwardly turned portions being adjacent each other when the pliers are closed; and the blunt edges of said grips adapted for engaging opposite sides of a tooth without damage thereto when the crown or inlay is positioned between said planar portions of the respective grips, and each said inwardly turned portion of the grips including one corner edge adapted for engagement under an edge of a crown or inlay to apply a lifting force thereto for removing the crown or inlay from the tooth.

2. The dental device of claim 1, wherein the edges of said grips are formed with indentions therein.

3. The dental device of claim 2, wherein said indentions are formed as semicircular cutouts.

4. The dental device of claim 2, wherein said indentions are formed in the respective edges of said grips so that when said edges are engaged together, the indentions in both edges together form respective openings.

5. The dental device of claim 4, wherein the indentions formed in said edges include valleys, and a portion of the edges that are engaged together form ridges, and wherein when all opposing edges are engaged together, the ridges engage together and the opposing valleys form said openings.

6. The dental device of claim 1, wherein said inwardly turned portion of each said grip is generally perpendicular to the respective blade.

7. The dental device of claim 1, wherein when the edges of said grips are engaged together, said grips form a U-shape from a side view, with a space between said blades.

8. The dental device of claim 1, wherein said grips are attached to the respective tips at an angle of between about 77 degrees and 87 degrees.

9. The dental device of claim 1, wherein a rubber material is coated on said grips.

10. The dental device of claim 9, wherein said rubber material is removable from said grips and is thus disposable.

11. The dental device of claim 1, wherein a plastic material is coated on said grips.

12. The dental device of claim 1, wherein said grips have a nonmetallic material formed on the edges of said grips that engage together.

13. The dental device of claim 1, further including a metal basket attached thereto at a location so as to catch an onlay or crown dislodged from the grips.

14. The dental device of claim 1, further including a mechanism for removably attaching the tips to said handles.

15. The dental device of claim 1, further including a mechanism for removably attaching the grips to said tips.

16. The device of claim 1, wherein said blades are formed with a curve to conform to and receive therebetween a tooth.

17. The device of claim 1, wherein said blades are formed as planar members.

18. A dental device, comprising:

a pliers having a pair of handles for operating a corresponding pair of tips, said handles attached together about an axis of pivotal movement, and said handles and tips extending generally horizontally and oriented generally perpendicular to said axis of rotation;

each said tip having a dog-leg shape portion when the device is viewed from a side thereof, and said tips are substantially spaced apart from each other when viewed from a top view of said device;

a grip attached to a respective end of each said tip, each said grip angled forwardly with respect to the dog-leg section so that the handles of said device can extend horizontally out of a patient's mouth while the grips are engaged with a back tooth of the patient;

each said grip formed as a blade of generally uniform thickness, and each said blade being generally parallel to each other;

each said blade terminating in with an inwardly turned tooth engaging portion with a blunt edge, the blunt edges of the inwardly turned portions being adjacent each other when the handles of the pliers are closed;

the blunt edges of said grips adapted for engaging opposite sides of a tooth without damage thereto when the crown or inlay is positioned between the blades of the respective grips, and each said inwardly turned portion of the grips including a corner edge adapted for engagement under an edge of a crown or inlay to apply a lifting force thereto for removing the crown or inlay from the tooth; and the blunt edge of each said blade including plural indentions formed therein, and wherein there is no indention in a center of each blunt edge of the blades.

* * * * *